United States Patent [19]

Bauer et al.

[11] Patent Number: 4,728,638
[45] Date of Patent: Mar. 1, 1988

[54] SOMATOSTATINE DERIVATIVES

[75] Inventors: Wilfried Bauer, Lampenberg; Janos Pless, Basil; René Huguenin, Reinach, all of Switzerland

[73] Assignee: Sandoz Ltd., Basel, Switzerland

[21] Appl. No.: 816,663

[22] Filed: Jan. 7, 1986

[30] Foreign Application Priority Data

Jan. 7, 1985 [CH] Switzerland .............................. 36/85
Mar. 28, 1985 [DE] Fed. Rep. of Germany ....... 3511206

[51] Int. Cl.$^4$ ......................... A61K 37/24; C07K 7/26
[52] U.S. Cl. ....................................... 514/11; 514/806; 514/17; 514/16; 530/311; 530/329
[58] Field of Search .................. 530/311, 329; 514/11, 514/806, 17, 16

[56] References Cited

U.S. PATENT DOCUMENTS

| 4,238,481 | 12/1980 | Rink et al. | 530/311 |
| 4,282,143 | 8/1981 | Sarantakis | 530/311 |
| 4,328,214 | 5/1982 | Rink et al. | 530/311 |
| 4,358,439 | 11/1982 | Sieber et al. | 530/311 |

Primary Examiner—Delbert R. Phillips
Attorney, Agent, or Firm—Gerald D. Sharkin; Robert S. Honor; Thomas O. McGovern

[57] ABSTRACT

Somatostatine derivatives of the general formula

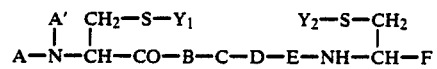

wherein either
(a)
A is

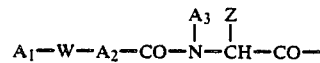

W is -CO-N($A_4$) or -N($A_5$)-CO- and
$Y_1$ and $Y_2$ are H or together a bond
or (b)
A is H, alkyl, phenylalkyl or RCO and
$Y_1$ and $Y_2$ are acyl groups as defined in claim 1, A', B, C, D, E, F, $A_1$, $A_2$, $A_3$, $A_4$, $A_5$, R and Z having the meanings recited in claim 1, have pharmacological, in particular GH-, gastric- and pancreatic secretion inhibiting activity.

10 Claims, No Drawings

SOMATOSTATINE DERIVATIVES

The present invention relates to novel somatostatines, processes for their production, pharmaceutical compositions containing them and their use as pharmaceuticals.

More particularly the present invention relates to polypeptides of formula I,

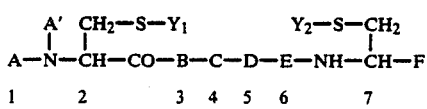

wherein either
(a) A is a residue of formula Ia

wherein
W is a group of formula

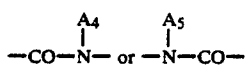

$A_1$ and $A_4$ are independently hydrogen, a saturated aliphatic $C_{1-19}$hydrocarbyl, unsaturated aliphatic $C_{2-19}$hydrocarbyl, or $C_{7-10}$phenylalkyl, wherein phenyl is optionally substituted by halogen, trifluoromethyl, nitro, hydroxy, $C_{1-3}$alkyl and/or $C_{1-3}$alkoxy, $A_5$ is hydrogen or a saturated aliphatic $C_{1-12}$hydrocarbyl or unsaturated $C_{2-12}$hydrocarbyl or $A_1 + A_5$ together signify tetramethylene or pentamethylene, $A_2$ is saturated $C_{1-19}$alkylene or unsaturated $C_{2-19}$alkylene, whereby $A_1$, $A_2$ and $A_4$ together or $A_1$, $A_2$ and $A_5$ together contain 10 to 20 carbon atoms, $A_3$ is hydrogen, a saturated aliphatic ($C_{1-12}$) hydrocarbyl, a unsaturated aliphatic ($C_{2-12}$)hydrocarbyl or ($C_{7-10}$)phenylalkyl, wherein phenyl is optionally substituted by halogen, trifluoromethyl, nitro, hydroxy, ($C_{1-3}$)alkyl or ($C_{1-3}$)alkoxy, >N—CH(Z)—CO— is
(1) an (L)- or (D)-phenylalanine residue optionally ring-substituted by halogen, $NO_2$, $NH_2$, OH, $C_{1-3}$alkyl and/or $C_{1-3}$alkoxy, or
(2) the residue of a natural α-amino acid other than defined under (1) above, or of a corresponding (D)-amino acid, whereby Z in >-N-CH(Z)-CO- represents the remainder of said residue (1) or (2).

A' is hydrogen and
$Y_1$ and $Y_2$ are each hydrogen or together represent a direct bond,
or (b)
A is hydrogen, $C_{1-12}$alkyl, $C_{7-10}$phenylalkyl or RCO,
R is hydrogen, $C_{1-12}$alkyl, phenyl or $C_{7-10}$phenylalkyl or
RCO is
(α) a (L)- or (D)-phenylalanine residue optionally ring-substituted by halogen, $NO_2$, $NH_2$, OH, $C_{1-3}$alkyl and/or $C_{1-3}$alkoxy or (β) the residue of a natural (L)-α-amino acid other than defined under (a) above, or of a corresponding (D)-amino acid or (γ) a dipeptide residue in which the individual amino acid residues are the same or different and are selected from those defined under (α) and (β) above, the α-amino group of amino acid residues (α) and (β) and the N-terminal amino group of dipeptide residues (γ) being optionally substituted by $C_{1-12}$alkyl or $C_{7-10}$phenylalkyl and/or $C_{1-11}$acyl.

A' is hydrogen or when A is ($C_{1-12}$)alkyl or ($C_{7-10}$)-phenylalkyl, then A' can also signify ($C_{1-12}$)alkyl whereby the total number of carbon atoms of A+A' does not exceed 13 carbon atoms.

$Y_1$ and $Y_2$ are independently a group of formula 1, 2, 3, 4 or 5,

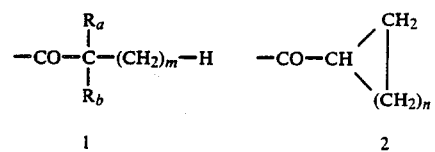

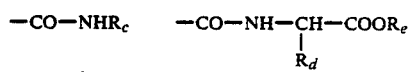

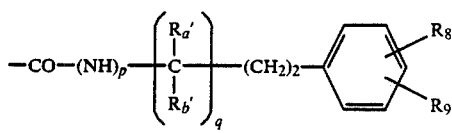

wherein
$R_a$ is methyl or ethyl,
$R_b$ is hydrogen, methyl or ethyl,
m is 1, 2, 3, 4 or
n is 1, 2, 3, 4 or 5
$R_c$ is ($C_{1-6}$)alkyl
$R_d$ represents the substituent attaching to the α-carbon atom of a natural α-amino acid (including hydrogen)
$R_e$ is ($C_{1-5}$)alkyl
$R_a'$ and $R_b'$ are independently hydrogen, methyl or ethyl,
$R_8$ and $R_9$ are independently hydrogen, halogen, ($C_{1-3}$)alkyl or ($C_{1-3}$)alkoxy,
p is 0 or 1,
q is 0 or 1,
r is 0, 1 or 2,
and for both cases (a) and (b)
B is —Phe— optionally ring-substituted by halogen, $NO_2$, $NH_2$, OH, $C_{1-3}$alkyl and/or $C_{1-3}$alkoxy,
C is (L)—Trp— or (D)—Trp— optionally α-N-methylated and optionally benzene-ring-substituted by halogen, $NO_2$, $NH_2$. OH, $C_{1-3}$alkyl and/or $C_{1-3}$alkoxy,
D is —Lys— optionally α-N-methylated,
E is Thr, Ser or Val
F is a group of formula —$COOR_1$, —$CH_2OR_2$,

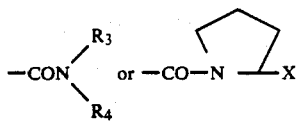

wherein
$R_1$ is hydrogen or $C_{1-3}$alkyl,
$R_2$ is hydrogen or the residue of a physiologically acceptable, physiologically hydrolysable ester,
$R_3$ is hydrogen, $C_{1-3}$alkyl, phenyl or $C_{7-10}$phenylalkyl, but when $R_4$ is $-CH(R_5)-X$ then $R_3$ is only hydrogen or methyl,
$R_4$ is hydrogen, $C_{1-3}$alkyl or a group of formula $-CH(R_5)-X$,
$R_5$ is hydrogen, $-(CH_2)_2-OH$ or $-(CH_2)_3-OH$, or represents the substituent attaching to the α-carbon atom of a natural α-amino acid and
X is a group of formula $-COOR_1$, $-CH_2OR_2$ or

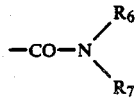

wherein
$R_1$ and $R_2$ have the meanings given above,
$R_6$ is hydrogen or $C_{1-3}$alkyl and
$R_7$ is hydrogen, $C_{1-3}$alkyl, phenyl or $C_{7-10}$phenylalkyl,
whereby the residues B, D and E have the L-configuration, and the residues in the 2- and 7-position and the residues $Y_1$4) and $Y_2$4) each independently have the (L)- or (D)-configuration, as well as the salt forms and complexes thereof.

A preferred group of compounds of formula I are those, wherein A, A', $Y_1$ and $Y_2$ have the meanings given under (a) above as well as the salt forms and complexes thereof.

Another preferred group of compounds of formula I are those, wherein A, A', $Y_1$ and $Y_2$ have the meanings given under (b) above as well as the salt forms and complexes thereof.

Throughout the present specification and claims by "halogen" is meant fluorine, chlorine and bromine. In accordance with conventional practice, amino acid residues referred to by abbreviation, e.g. —Phe—, —Cys— etc., are to be understood as having the (L)-configuration unless otherwise indicated. The term natural amino acid refers to amino acids derived from natural sources or produced otherwise e.g. by synthesis or cell culture.

In the N-Acylpolypeptides of formula I, wherein A means the group of formula Ia, the aliphatic groups $A_1-A_5$ may be saturated or unsaturated, branched- or straight-chain. Similarly alkyl, alkenyl and alkinyl groups as well as the alkyl-moieties of phenylalkyl groups recited may all be branched- or straight-chain. All groups recited as $A_1-A_5$ may optionally bear further substituents. Suitably groups recited as $A_1-A_5$ are unsubstituted.

In these N-Acyl-polypeptides, the following significances or combinations thereof are preferred:
$A_1+A_2+A_4$ or $A_1+A_2+A_5$ contain 12 to 14 carbon atoms.
$A_3$ is hydrogen or methyl, especially hydrogen.

When $>N-CH(Z)-CO-$ has the meaning (1), it is preferably an (L)- or (D)-phenylalanine or (L)- or (D)-tyrosine residue (whereby Z is benzyl or p—OH—benzyl), most preferably a (D)-phenylalanine residue.

When $>-N-CH(Z)-CO-$ has the meaning (2), the defined residue is preferably lipophilic. Preferred residues (2) are accordingly residues in which Z is alkyl having 3, preferably 4, or more carbon atoms.

Most preferably $>-N-CH(Z)-CO-$ has the meaning (1).

Preferably $Y_1$ and $Y_2$ together represent a direct bond.

In the polypeptides of formula I, wherein A has the meanings given above under (b), the acyl residues, with which the N-terminal amino group of RCO may be acylated include, in particular, the acyl residues of organic carboxylic acids, sulfonic acids, sulfaminic acids and carbonic acids and their derivatives. Suitable acylresidues are, e.g. the groups:

1. $R_0CO$ wherein $R_0$ is a saturated or unsaturated, branched- or straight-chain, optionally substituted aliphatic, or cycloaliphatic group, an aromatic or heterocyclic group, especially saturated $C_{1-10}$alkyl, $C_{2-10}$alkenyl, $C_{2-10}$alkinyl, phenyl, naphthyl or $C_{7-10}$phenylalkyl.

2. $R'SO_2-$ wherein $R'$ is $C_{1-10}$alkyl, phenyl or $C_{7-10}$(phenylalkyl)

3. $R''O-CO-$ wherein $R''$ is $C_{1-10}$alkyl or $C_{7-10}$(phenylalkyl)

4.

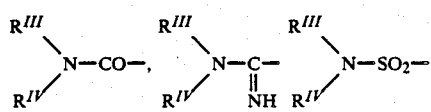

wherein
$R^{III}$ is hydrogen, $C_{1-10}$alkyl, phenyl or $C_{7-10}$(phenylalkyl) and
$R^{IV}$ is hydrogen or $C_{1-10}$alkyl
whereby the total number of carbon atoms in $R^{III}+R^{IV}$ does not exceed 10.

5. $A_1-W-A_2-CO$ wherein $A_1$, W and $A_2$ are as defined above and the total number of carbon atoms in $A_1-W-A_2$ does not exceed 10.

In the polypeptides of formula I, wherein A has the meanings given above under (b), A is preferably RCO.

RCO is preferably phenylpropionyl or optionally monomethylated, monobenzylated or acylated D—Phe.

$Y_1$ and $Y_2$ have preferably the meanings given under (1) and (3), more preferably the meaning given under (1), and are especially tert. butyl.

In the compounds of formula I, the following significances or combinations thereof are furthermore preferred:
B is Phe or Tyr
C is —(D) Trp
D is Lys
E is Thr
F is

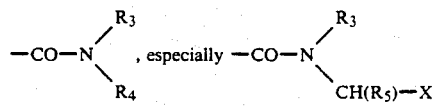

wherein $R_3$ is hydrogen, $R_5$ is $CH_2OH$, $CH(CH_3)OH$, i-butyl, $CH_2CH_2OH$ or $(CH_2)_3OH$, preferably $CH_2OH$ or $CH(CH_3)OH$, especially $CH(CH_3)OH$, X is

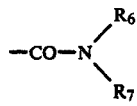

or $CH_2OR_2$, especially $CH_2OR_2$, $R_2$ is hydrogen $R_2$ as an acid residue is preferably formyl, $C_{2-12}$alkylcarbonyl, $C_{8-12}$phenylalkylcarbonyl or benzoyl the group $-CH(R_5)-X$ has preferably L-configuration.

Preferably the residues in the 2- and 7-positions have the L-configuration.

The compounds of formula I may exist in salt form or in the form of complexes thereof. Acid addition salts may be formed with e.g. organic acids, polymeric acids and inorganic acids. Such acid addition salt forms include e.g. the hydrochlorides and acetates. By complexes are to be understood compounds of know type, formed from compounds of formula I on addition of inorganic substances, e.g. inorganic salts or hydroxides such as Ca— and Zn—salts, and/or on addition of polymeric organic substances.

The present invention in another aspect provides a process for the production of compounds according to the invention. These compounds may be produced by methods known in the art of peptide chemistry or by obvious chemical equivalents thereof, for example by a process comprising (a) removing the protecting group or groups from a protected polypeptide having the sequence indicated in formula I, (b) linking together by an amide bond two peptide units, each of which contains at least one amino acid or amino alcohol residue in protected or unprotected form and one peptide unit containing a N-terminal acyl residue or one or two peptide units containing S—acyl residues, the peptide units being such that a protected or unprotected polypeptide having the sequence indicated in formula I is obtained and, if necessary, carrying out process step (a):

(c) converting the group F of a protected or unprotected polypeptide having the sequence indicated in formula I, into another group F, and, if necessary carrying out process step (a);

(d) oxidising a compound of formula I, wherein A is a residue of formula Ia and the mercapto groups of the Cys—residues are in free form to provide a polypeptide, wherein $Y_1$ and $Y_2$ together are a direct bond, and recovering the polypeptide thus obtained in free or salt form or as a complex thereof.

The above process may for example be carried out analogously to the processes described in the accompanying examples. Insofar as the production of the starting materials is not particularly described, the compounds are known or may be produced and purified in accordance with methods known in the art.

Amino acids or peptides which are acylated on the α-N-atom can be prepared by acylating the corresponding amino acids or peptides in conventional manner e.g. using reactive acid derivatives or isocyanates. The introduction of groups $Y_1$ and $Y_2$ into the SH—groups of the Cys—residues in the positions 2 and 7 can be effected in conventional manner for acylation reactions, e.g. by reacting a polypeptide containing a free SH-group with a reactive acid derivative, especially an acid halide, to introduce the residues (1), (2) and (5) (wherein p=0) as defined above for $Y_1$ and $Y_2$) or with an isocyanate to introduce the residues (3), (4) and (5) (wherein p=1) as defined above for $Y_1$ and $Y_2$). Compounds, wherein $Y_1$ and $Y_2$ have the meaning (4) can be prepared by employing isocyanates of amino acids, which can be obtained in known manner, e.g. by reacting an amino acid with phosgene and removal of HCl.

In the following examples all temperatures are given in degrees Centigrade and are uncorrected.

In the following examples except where otherwise indicated $[\alpha]_D^{20}$ values are uncorrected minimum values, the product generally containing varying amounts of water, salts and/or acetic (hydrochloric) acid. The following abbreviations are employed:

| | | |
|---|---|---|
| AcOH | = | acetic acid |
| BOC | = | tert.-butoxycarbonyl |
| BTFA | = | boron-tris-trifluoroacetate |
| DCCI | = | dicyclohexylcarbodiimide |
| DMF | = | N,N—dimethylformamide |
| HOBT | = | N—hydroxybenzotriazole |
| MBzl | = | p-methoxybenzyl |
| Me | = | methyl |
| MeOH | = | methanol |
| $NEt_3$ | = | triethylamine |
| ONP | = | 4-Nitrophenoxy |
| TFA | = | trifluoroacetic acid |
| THF | = | tetrahydrofuran |
| Thr—ol | = | the threoninol residue 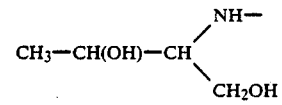 |
| Z | = | benzyloxycarbonyl |

EXAMPLE 1

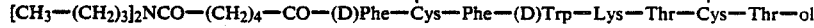

0.74 g $[CH_3-(CH_2)_3]_2NCO-(CH_2)_4-CO-(D)$-Phe—Cys(MBzl)—Phe—(D)Trp—Lys(Z)—Thr—Cys(MBzl)—Thr—Ol and 5 ml thioanisole are dissolved in 5 ml TFA at 0° C. The solution is cooled to −10° C., 12 ml ca. 2M BTFA in TFA are added and the solution is stirred for 1.5 hours at −5° C. The obtained reaction mixture is then treated under stirring with 50 ml abs. MeOH at −60°. A mixture of 12 ml HCl/ethylether (∼5N) in 1,5 liters ethyl ether are added under stirring.

The precipitated product is filtered off, washed with ethyl ether and dissolved immediately in 3 liters of dioxane/$H_2O$ (7:3). 1N $NH_4OH$ is added with stirring until the pH reaches 7.5 to 8.0 and the solution is stirred in an open vessel at room temperature until testing for —SH groups (e.g. by the Ellmann-method) is negative.

The pH is adjusted to ~4 by addition of dilute HCl, the solution concentrated under vacuum and lyophilised. The raw product is purified chromatographically on silica gel using a mixture of CHCl$_3$/MeOH/glacial AcOH/H$_2$O as eluant. Fractions containing the desired product are combined, diluted with H$_2$O, concentrated and lyophilised to yield the title compound (as the acetate): $[\alpha]_D^{20} = -33°$ (c=0.45 in 95% AcOH).

The starting material is produced as follows:

(a) BOC—Cys(MBzl)—Phe—(D)Trp—Lys(Z)—Thr—Cys(MBzl)—Thr—ol 3.6 g H—Phe—(D)Trp—Lys(Z)—Thr—Cys(MBzl)—Thr—ol—hydrochloride in 40 ml DMF are treated with 0.44 ml NEt$_3$, followed by 1.6 g BOC—Cys(MBzl)—ONP. The mixture is stirred at room temperature for 15 hours, then concentrated under vacuum and diluted with MeOH. Water is added until the product precipitates. The precipitate is filtered, washed with MeOH and dried to yield the heading compound: $[\alpha]_D^{20} = -15.5°$ (c=1.0 in DMF); m.p. 175°.

(b) H—Cys(MBzl)—Phe—(D)Trp—Lys(Z)—Thr—Cys(MBzl)—Thr—ol—hydrochloride 3.5 g BOC—Cys(MBzl)—Phe—(D)Trp—Lys(Z)—Thr—Cys(MBzl)—Thr—ol are dissolved in 25 ml TFA/H$_2$O (9:1) at 0° and the mixture stirred for 45 minutes at 0°. The reaction mixture is stirred into a mixture comprising 500 ml ethyl ether and 5 ml HCl in ethyl ether (~5N) and the precipitated product filtered off, washed with ethyl ether and dried to yield the heading compound: $[\alpha]_D^{20} = -16°$ (c=1.0 in 95% AcOH), dec. at 120°.

[CH$_3$—(CH$_2$)$_3$]$_2$NCO(CH$_2$)$_4$COOH 15 g adipic acid, 17.3 ml di-n-butylamine and 14 g HOBT in 1.9 l DMF are pre-cooled to $-10°$ and treated with 22 g DCCI in 50 ml DMF. The mixture is stirred for ca. 20 hours at 0°, then 80 hours at room temperature and filtered. The filtrate is concentrated under vacuum. The residue is purified by chromatography eluting with CH$_2$Cl$_2$/MeOH. Fractions containing the desired product are collected and evaporated to give the heading compound as an oil.

(d) [CH$_3$(CH$_2$)$_3$]$_2$NCO—(CH$_2$)$_4$—CO—(D)Phe—NH—NH—BOC 2.0 g of the compound of step (c) and 0.97 g p-nitrophenol in 50 ml ethyl acetate are pre-cooled to $-10°$ and treated with a solution of 1.5 g DCCI in 5 ml ethyl acetate. The mixture is stirred for 4 hours at 0°, then for 15 hours at room temperature and filtered. The filtrate is evaporated under vacuum to give an "active ester" which is used without further purification.

2.8 g of the "active ester", 2.1 g H—(D)—Phe—NH—NH—BOC and 1.0 g HOBT in 40 ml DMF are stirred ca. 20 hours at room temperature. The mixture is concentrated under vacuum, the residue diluted with ethyl ether and washed with 2N citric acid, Na$_2$CO$_3$ solution and H$_2$O. The organic phase is dried over Na$_2$SO$_4$ and evaporated under vacuum, whereby the heading compound is obtained as a foam: $[\alpha]_D^{20} = +12.6°$ (c=0.8 in DMF).

(e) [CH$_3$—(CH$_2$)$_3$]$_2$NCO(CH$_2$)$_4$CO—(D)Phe—NH—NH$_2$-hydrochloride 3 g of the product of step (d) are dissolved in 10 ml 95% TFA and the solution allowed to stand for 1 hour at room temperature. The reaction mixture is stirred into a mixture of 500 ml ethyl ether and 4 ml HCl in ethyl ether (~5N) and the precipitated product filtered off, washed with ethyl ether and dried to yield the heading compound: $[\alpha]_D^{20} = +4.7°$ (c=0.5 in 95% AcOH).

(f) [CH$_3$—(CH$_2$)$_3$]$_2$NCO—(CH$_2$)$_4$CO—(D)-Phe—Cys(MBzl)—Phe—(D)Trp—Lys(Z)—Thr—Cys(MBzl)—Thr—ol 1 ml ca. 5N HCl in ether are added with stirring to 0.35 g of the product of step e) in 15 ml DMF pre-cooled to $-20°$, followed by 0.95 ml 10% tert.butylnitrite in DMF. The mixture is stirred for 20 minutes at $-15°$ and treated with 0.70 ml NEt$_3$ at $-20°$, followed by a cold solution of 0.8 g H—Cys(MBzl)—Phe—(D)Trp—Lys(Z)—Cys(MBzl)—Thr—ol hydrochloride and 0.1 ml NEt$_3$ in 5 ml DMF. The mixture is stirred for 16 hours at $-5°$ and for a further 5 hours at 0°. The pH is adjusted to 8.5-9 by the addition of NEt$_3$ and then diluted with ca. 200 ml MeOH. The product is precipitated by addition of H$_2$O. The precipitate is filtered off, washed with H$_2$O/MeOH (1:1) and dried to yield the heading compound, m.p. 190°, $[\alpha]_D^{20} = -19.7°$ (c=0.6 in DMF).

EXAMPLE 2

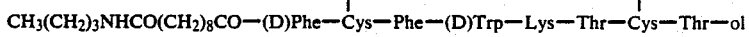

CH$_3$(CH$_2$)$_3$NHCO(CH$_2$)$_8$CO—(D)Phe—Cys—Phe—(D)Trp—Lys—Thr—Cys—Thr—ol

In manner analogous to that described in Example 1 and using as starting material CH$_3$—(CH$_2$)—NHCO(CH$_2$)$_8$CO—(D)Phe—Cys(MBzl)—Phe—(D)Trp—Lys(Z)—Thr—Cys(MBzl)—Thr—ol the title compound is obtained (as the acetate) M.p. = 178° (decomp.) $[\alpha]_D^{20} = -28,5°$ (c=0,61 in 95% AcOH).

The starting material is produced as follows:

(a) CH$_3$—(CH$_2$)$_3$—NHCO—(CH$_2$)$_8$COOH

In manner analogous to that described in Example 1(c) the heading compound, m.p. 146° is obtained.

(b) BOC—(D)Phe—Cys(MBzl)—Phe—(D)Trp—Lys(Z)—Thr—Cys(MBzl)—Thr—ol 0.7 g HOBT and 1.75 g BOC—(D)Phe—Cys(MBzl)—Oh are added to 3.6 g H—Phe—(D)Trp—Lys(Z)—Thr—Cys(MBzl)—Thr—ol—hydrochloride and 0.5 ml NEt$_3$ in 90 ml DMF. The mixture is cooled to $-10°$ and 0.76 g DCCI in 4 ml DMF are added. The reaction mixture is stirred for ca. 15 hours at 0° and 10 hours at room temperature, filtered and the filtrate is concentrated under vacuum, diluted with MeOH and H$_2$O added until precipitation occurs. After filtration the residue is washed with MeOH/H$_2$O and dried to give the heading compound: $[\alpha]_D^{20} = -22°$ (c=0.5 in DMF), m.p. 175°.

(c) H—(D)Phe—Cys(MBzl)—Phe—(D)Trp—Lys(Z)—Thr—Cys(MBzl)—Thr—ol 3.6 g of the compound of step (b) are dissolved at 0° in TFA/H$_2$O (9:1) and the solution stirred for 20 minutes at room temperature. The reaction mixture is stirred into a mixture comprising ca. 400 ml ethyl ether and 2 ml HCl in ethyl ether (~5N) and the precipitated product filtered off, washed with ethyl ether and dried to yield the heading compound, decomp. from 130°, $[\alpha]_D^{20} = -33°$ (c=0.5 in 95% AcOH).

(d) $CH_3-(CH_2)_3-NHCO(CH_2)_8CO-(D)Phe-Cys(MBzl)-Phe-(D)Trp-Lys(Z)-Thr-Cys(MBzl)-Thr-ol$

A solution of 1.76 g of the compound of step (c), 0.25 ml ethyldiisopropyl-amine, 0.21 g HOBT and 0.3 g of the compound of step (a) in 10 ml DMF is cooled to $-10°$ and treated with 0.28 g DCCI in 2 ml DMF. The mixture is stirred for 15 hours at 0°, then 25 hours at room temperature. The mixture is filtered, and the filtrate diluted with MeOH. 2 ml of 1N HCl and $H_2O$ are added until precipitation occurs. After filtration the residue is washed with MeOH/$H_2O$ and dried to give the heading compound: $[\alpha]_D^{20}=-17.6°$ (c=0.66 in DMF).

EXAMPLE 3

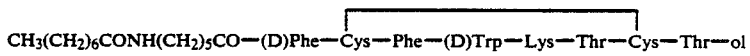

is produced as the acetate analogously to Example 1, $[\alpha]_D^{20}=-27.3°$ (c=0.71 in 95% AcOH)(content of the title compound: 76%, 1st batch)—with further adsorption chromatography to remove salts $[\alpha]_D^{20}=-38.6°$ (c=1.08 in 95% AcOH), (content of the title compound: 90%, 2nd batch).

Intermediates:

$CH_3(CH_2)_6CONH(CH_2)_5CO-(D)Phe-Cys(MBzl)-Phe-(D)Trp-Lys(Z)-Thr-Cys(MBzl)-Thr-ol$, M.p.: 193°–195°, $[\alpha]_D^{20}=-20,0°$ (c=0,80 in DMF) produced analogously to Example 1(f).

$CH_3(CH_2)_6CONH(CH_2)_5CO-(D)Phe-NH-NH_2$—hydrochloride, M.p. from 176°, produced analogously to Example 1(e).

$CH_3(CH_2)_6CONH(CH_2)_5CO-(D)Phe-NH-NH-BOC$, produced analogously to example 1(d), obtained as a foam, $[\alpha]_D^{20}=+10,6°$ (c=0.5 in DMF), M.p. 105° C.

$CH_3(CH_2)_6CONH(CH_2)_5COOH$, produced from $CH_3(CH_2)_6COCl$ and $H_2N-(CH_2)_5COOH$ according to the Schotten-Baumann reaction. M.p. 64° C.

The following compounds may be produced analogously to Examples 1–3:

TABLE 1

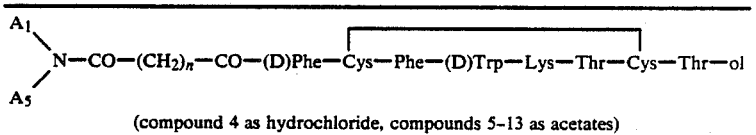

(compound 4 as hydrochloride, compounds 5-13 as acetates)

| Example No. | $A_1$ | $A_5$ | n | $[\alpha]_D^{20}$ in 95% AcOH |
|---|---|---|---|---|
| 4 | $C_2H_5$ | $C_2H_5$ | 8 | $-37.6°$ (c = 0.7) |
| 5 | phenyl-$CH_2$ | H | 8 | $-22.5°$ (c = 0.6) |
| 6 | $(CH_2)_4$ (cyclic) | | 8 | $-29.2°$ (c = 0.5) |
| 7 | $CH_3$ | $CH_3$ | 12 | $-29.1°$ (c = 0.2) |
| 8 | $CH_3(CH_2)_9$ | H | 2 | $-36.0°$ (c = 1.0) |
| 9 | $CH_3(CH_2)_5$ | $CH_3(CH_2)_5$ | 2 | $-38.0°$ (c = 1.0) |
| 10 | $CH_3(CH_2)_3$ | $CH_3(CH_2)_3$ | 6 | $-30.0°$ (c = 1.0) |
| 11 | $CH_3(CH_2)_6$ | H | 6 | $-25.3°$ (c = 1.1) |
| 12 | $CH_3(CH_2)_4$ | $CH_3(CH_2)_4$ | 4 | $-37.0°$ (c = 1.0) |
| 13 | $CH_3(CH_2)_3$ | $CH_3(CH_2)_3$ | 5 | $-34.0°$ (c = 1.0) |

TABLE 2

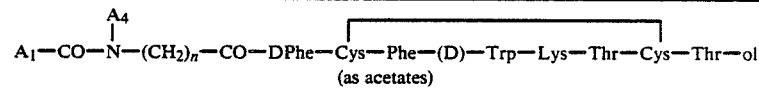

(as acetates)

| Example No. | $A_1$ | $A_4$ | n | $[\alpha]_D^{20}$ in 95% AcOH |
|---|---|---|---|---|
| 14 | $CH_3(CH_2)_6$ | H | 7 | $-26,3°$ (c = 1.0) |
| 15 | $CH_3(CH_2)_6$ | $CH_3$ | 5 | $-29.0°$ (c = 1.0) |
| 16 | phenyl-$(CH_2)_2$ | H | 4 | $-30.8°$ (c = 1.0) |
| 17 | phenyl-$(CH_2)_3$ | H | 5 | $-32.0°$ (c = 1.0) |

EXAMPLE 8

$H-(D)Phe-Cys[COC(CH_3)_3]-Phe-(D)Trp-Lys-Thr-Cys[COC(CH_3)_3]-Thr-ol$ (a)

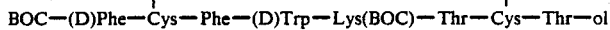

0.50 g

in 10 ml DMF are treated with 0.14 ml NEt₃, then with 0.22 ml (BOC)₂O and the mixture left for 16 hours at room temperature. Ethyl ether/diisopropyl ether are added and the precipitate filtered off and dried to yield the heading compound. $[\alpha]_D^{20} = +10°$ (c=1.0 in DMF).

(b) BOC—(D)Phe—Cys—Phe—(D)Trp—Lys(BOC-)—Thr—Cys—Thr—ol 0.18 g Dithioerythritol are added to 0.4 g of the compound of step (a) in 7 ml dioxane and 3 ml 1 m NEt₃./AcOH buffer pH 8.6 under argon. The mixture is stirred for 15 hours at room temperature, diluted with MeOH/H₂O and the precipitated product filtered off, washed with MeOH/H₂O and dried to yield the heading compound, m.p. 220°. $[\alpha]_D^{20} = -46.2°$ (c=1.0 in pyridine).

(c) BOC—(D)Phe—Cys[COC(CH₃)₃]—Phe—(D)Trp—Lys(BOC)—Thr—Cys[COC(CH₃)₃]—Thr—ol 0.2 g of the product of step (b) are dissolved under argon at 0° in 15 ml N-methyl-pyrrolidone and treated with 0.16 ml N-methylmorpholine and 0.2 ml pivaloyl chloride.

The reaction mixture is stirred for 16 hours at 0°, then stirred into diisopropyl ether/hexane and centrifuged. The residue is dissolved in DMF and precipitated with MeOH/H₂O. After centrifugation the residue is dried and used for the next step. (d) H—(D)Phe—Cys[-COC(CH₃)₃]—Phe—(D)Trp—Lys—Thr—Cys[-COC(CH₃)₃]—Thr—ol The product of step (c) is dissolved at B 0° in 5 ml TFA/H₂O (9:1) and then stirred for 30 minutes at room temperature. After dilution with a mixture of 100 ml ethyl ether and 1 ml HCl in ethyl ether (5N) the precipitated product is separated by centrifugation, washed with ethyl ether and dried. The precipitate is purified by chromatography on silica gel eluting with CHCl₃/MeOH/AcOH/H₂O. The fractions containing the desired product are collected, concentrated under vacuum and lyophilised, to yield the heading compound (as the acetate): $[\alpha]_D^{20} = -25.4°$ (c=0.5 in 95% AcOH).

EXAMPLE 19

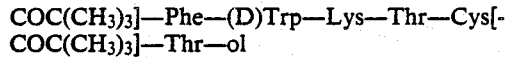

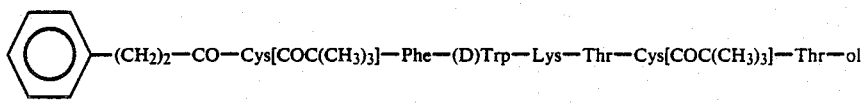

(a)

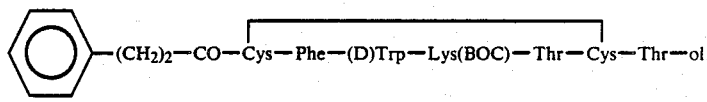

2,2 g

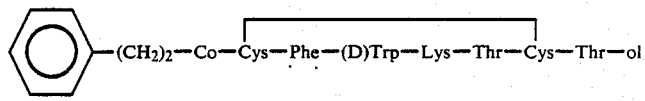

in 30 ml DMF are treated with 0.3 ml NEt₃ followed by 0.48 ml (BOC)₂O. The mixture is stirred for 15 hours at room temperature, stirred into ethyl ether and filtered. The residue is dissolved in a small quantity of DMF/MeOH.

H₂O is added until the product precipitates. After filtration the residue is washed with MeOH/H₂O and dried to yield the heading compound, m.p. 160°. $[\alpha]_D^{20} = +4,5°$ (c=1.0 in DMF).

(b)

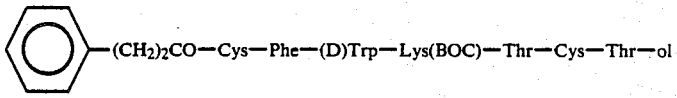

1.4 g Dithioerythritol are added to 2.0 g of the compound of step (a) in 50 ml dioxane and 10 ml 1 m NEt₃./AcOH buffer pH 8.6 under argon. The mixture is stirred for 15 hours at room temperature and concentrated under vacuum. After addition of MeOH the mixture is centrifuged. The residue is stirred with MeOH, centrifuged and dried under vacuum to yield the heading compound. $[\alpha]_D^{20} = -6.6°$ (c=1.0 in DMF).

(c)

—(CH$_2$)$_2$CO—Cys—[COC(CH$_3$)$_3$]—Phe—(D)Trp—Lys(BOC)—Thr—Cys[COC(CH$_3$)$_3$]—Thr—ol 0.4 g of the product of step (b) are dissolved under argon in 30 ml N-methyl-pyrrolidone and treated at 0° with 0.41 ml N-methl-morpholine and 0.42 ml pivaloyl chloride. The reaction mixture is stirred at 0° for 18 hours, and then stirred into diisopropyl ether and hexane. The precipitate is separated by centrifugation, the residue is dissolved in a small volume of DMF and precipitated by addition of MeOH and H$_2$O. After centrifugation the residue is dried under vacuum and purified by chromatography on silica gel eluting with CH$_2$Cl$_2$/MeOH. The fractions containing the desired product are collected and concentrated under vacuum. Diisopropyl ether/hexane are added until the product precipitates. After centrifugation the heading compound is obtained. $[\alpha]_D^{20} = -26°$ (c=1.0 in DMF).

(d)

—(CH$_2$)$_2$CO—Cys[CONH(CH$_2$)$_3$CH$_3$]—Phe—(D)Trp—Lys—Thr—Cys—[CONH(CH$_2$)$_3$CH$_3$]—Thr—ol is centrifuged off, the residue is stirred with diisopropyl ether, centrifuged and dried to yield the title compound. $[\alpha]_D^{20} = -23°$ (c=1.0 in DMF).

(b)

0.26 g of the product of step (a) are dissolved at 0° in 4 ml TFA/H$_2$O (9:1) and then stirred at room temperature for 30 minutes. The mixture is stirred into a mixture of 100 ml ethyl ether and 1 ml HCl in ethyl ether (~5N), the precipitated product centrifuged, washed with ethyl ether, dried and chromatographed on silica gel eluting with CHCl$_3$/MeOH/AcOH/H$_2$O. The fractions containing the desired product are collected, concentrated under vacuum and lyophilised to yield the heading compound (as the acetate): $[\alpha]_D^{20} = -17.3°$ (c=0.5 in 95% AcOH).

In manner analogous to the Example 18 or 20 and

—(CH$_2$)$_2$CO—Cys[COC(CH$_3$)$_3$]—Phe—(D)Trp—Lys—Thr—Cys[COC(CH$_3$)$_3$]—Thr—ol In manner analogous to Example 18(d) and using the Example 19(c) compound, the heading compound is obtained. $[\alpha]_D^{20}$ $-22°$ (c=1.0 in 95% AcOH).

EXAMPLE 20

—(CH$_2$)$_2$CO—Cys[CONH(CH$_2$)$_3$CH$_3$]—Phe—(D)Trp—Lys—Thr—Cys—[CONH(CH$_2$)$_3$CH$_3$]Thr—ol (a)

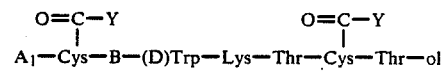

—(CH$_2$)$_2$CO—Cys[CONH(CH$_2$)$_3$CH$_3$]—Phe—(D)Trp—Lys(BOC)—Thr—Cys—[CONH(CH$_2$)$_3$CH$_3$]—Thr—ol 0,4 g of the product of step 19(b) in 20 ml DMF are treated under argon at 0° with 0.14 ml n-butylisocyanate. The mixture is stirred at 0° for 15 hours and then stirred into diisopropylether. The precipitated product using appropriate starting materials the following compounds of formula are prepared:

|    | A$_1$ | B | Y | $[\alpha]_D^{20}$ | (c in 95% AcOH) |
|----|-------|---|---|-------------------|------------------|
| 21 | H—(D)Phe | Phe |  | $-23.2°$ | 0.5 a |
| 22 | H—(D)Phe | Phe | —CH(CH$_3$)$_2$ | $-33°$ | 0.5 b |
| 23 | H—(D)Phe | Phe | NH(CH$_2$)$_3$CH$_3$ | $-24.4°$ | 1.0 a |
| 24 | H—(D)Phe | PHe | NHCH$_2$CH$_3$ | $-24°$ | 1.0 a |

-continued

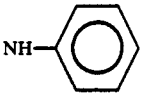

| | A₁ | B | Y | $[\alpha]_D^{20}$ | (c in 95% AcOH) |
|---|---|---|---|---|---|
| 25 | H—(D)Phe | PHe | NH—⟨Ph⟩ | −32° | 1.0 b |
| 26 | H—(D)Phe | Tyr | NH(CH₂)₃—CH₃ | −31.5° | 0.5 b |
| 27 | ⟨Ph⟩—(CH₂)₂—CO | Tyr | NH(CH₂)₃—CH₃ | −13.5 | 0.5 b |
| 28 | H—(D)Phe | Phe | Gly—OCH₃ | −28° | 0.5 a |
| 29 | H—(D)Phe | Phe | Phe—OCH₃ | −13° | 0.5 b |
| 30 | ⟨Ph⟩—(CH₂)₂—CO | Tyr | —C(CH₃)₃ | −23° | 1,0 b |
| 31 | H—(D)Phe | Tyr | —C(CH₃)₃ | −27° | 1,0 b | a: as acetate
b: as hydrochloride

The polypeptides of formula I as well as their pharmaceutically acceptable salts and complexes exhibit valuable pharmacological properties as indicated in animal tests. In particular they exhibit GH-secretion inhibiting activity as indicated e.g. by depression of serum GH-levels in the rat.

This test is carried out employing male rats. The test-substance is administered at varying, logarithmically staggered doses employing at least 5 rats per dose. 1, 6 and 18 hours after the administration of the test substance blood is taken. The determination of the serum GH-level is effected by radio-immuno-assay. The compounds of formula I are active in this test when administered at a dosage in the range of from 0.01 to 50 µg/kg s.c.

The compounds of formula I are accordingly useful in the treatment of disorders with an aetiology comprising or associated with excess GH-secretion, e.g. in the treatment of diabetes mellitus, angiophathy and proliferative retinopathy as well as of acromegaly.

For this use the dosage will, of course, vary depending on the compound employed, mode of administration and treatment desired. However, in general, satisfactory results are obtained when administered at a daily dosage of from about 0.01 to about 150 µg/kg animal body weight. For the larger mammals an indicated daily dosage is in the range from about 2 µg to about 10 mg of the compound conveniently administered in divided doses 2 to 4 times a day in unit dosage form containing for example from about 0.5 µg to about 5 mg of the compound or in sustained release form.

The polypeptides of formula I, their salts and complexes also inhibit gastric—and pancreatic secretion as indicated in standard animal tests. They are thus useful in the treatment of gastro-intestinal disorders, for example in the treatment of gastric ulcer, gastro-intestinal bleeding, acute pancreatitis and gastro-intestinal hormone secreting tumours (e.g. vipomas, glucagonomas, insulinomas, carcinoids and the like).

The compounds of the invention are also effective in inhibiting the proliferation and/or keratinisation of epidermal the proliferation and/or keratinisation of epidermal cells and are thus useful in the treatment of dermatological diseases involving morbid proliferation and/or keratinisation of epidermal cells, in particular in the treatment of psoriasis.

Furthermore the compounds of the invention are useful also in the treatment of degenerative senile dementia, also known as senile dementia of the Alzheimer type (SDAT), as well as of cluster headache.

For the above uses, the dosage required will of course vary depending on e.g. the particular compound employed, the mode of administration, the particular condition to be treated and the effect desired. In general, satisfactory results are obtained when administered at a daily dosage of about 0.01 to 150 µg/kg animal body weight. For the larger mammals an indicated daily dosage is in the range from about 2 µg to about 10 mg of the compound conveniently administered in divided doses 2 to 4 times a day in unit dosage form containing for example from about 0.5 µg to about 5 mg of the compound or in sustained release form.

The compounds of formula I may be administered in similar manner to known standards for use in the recited indications, e.g. somatostatine in the case of GH lowering activity e.g. for acromegaly or gastro-intestinal bleeding. As previously indicated a suitable daily dosage for any particular compound will depend on a number of factors including its relative potency of activity.

Thus the ID₅₀ of the compound of Example 3 as determined in the above-mentioned GH-sceretion inhibiting test after 1 hour is 0.06 µg/kg s.c. and that of Example 19 0.27 µg/kg s.c. compared with a measured ID₅₀ of 950 µg/kg s.c. for the natural somatostatine. The compounds show further a long-lasting activity.

Thus the ID₅₀ after 6 hours of the Example 3 compound is 3.0 µg/kg s.c. and of the Example 19 compound 0.7 µg/kg s.c. The ID₅₀ of natural somatostatine is after 6 hours extremely high and therefore not determinable.

The compounds of examples 3 and 19 are therefore indicated to be administered s.c. at doses about 15,000 or 3,500 times respectively less than somatostatine.

The Example 3 compound is the preferred compound.

The GH-secretion inhibiting utility is the preferred utility.

The compounds of formula I may also be administered in free form or in pharmaceutically acceptable acid addition salt form or complexes. Such salts and complexes may be prepared in conventional manner and exhibit the same order of activity as the free compounds. The present invention also provides a pharmaceutical composition comprising a compound of formula I in free base form or in salt form in association with a pharmaceutically acceptable diluent or carrier. Such compositions may be formulated in conventional manner. The compounds may be administered by any conventional route in particular preferably parenterally e.g. in form of injectable solutions or suspensions.

In accordance with the foregoing the present invention further provides:

(1) a method of treating disorders with an aetiology comprising or associated with excess GH-secretion (such as diabetes mellitus, angiopathy and acromegaly), of treating gastro-intestinal disorders (such as gastric ulcer, gastro-intestinal bleeding, acute pancreatitis and gastro-intestinal hormone secreting tumours) of inhibiting the proliferation and/or keratinisation of epidermal cells (such as psoriasis) as well as of treating degenerative senile dementia or cluster headache in a subject in need of such treatment, which method comprises administering to said subject an effective amount of a polypeptide in accordance with the invention or of a pharmaceutically acceptable salt or complex thereof and (2) pharmaceutical compositions comprising a polypeptide in accordance with the invention or a pharmaceutically acceptable salt or complex thereof, together with a pharmaceutically acceptable diluent of carrier therefor.

In one group of compounds of formula I, A is residue of formula Ia, wherein
W is a group of formula

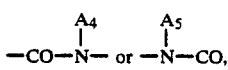

$A_1$ is saturated aliphatic $C_{1-19}$hydrocarbyl or $C_{7-10}$phenylalkyl $A_4$ is hydrogen or saturated aliphatic $C_{1-19}$hydrocarbyl $A_5$ is hydrogen or saturated aliphatic $C_{1-12}$hydrocarbyl $A_2$ is saturated $C_{1-19}$alkylene $A_3$ is hydrogen >—N—CH(Z)—CO— is (D)-phenylalinine residue A' is hydrogen $Y_1$ and $Y_2$ together represent a direct bond B is Phe C is —(D)Trp D is Lys E is Thr F is

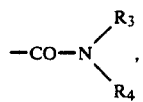

wherein
$R_3$ is hydrogen $R_4$ is —CH($R_5$)—X,
$R_5$ is CH(CH$_3$)OH
X is CH$_2$OH
as well as the salt forms thereof.

In another group of compounds of formula I
A is RCO, wherein R is $C_{7-10}$phenylalkyl or A is (D)-phenylalanine
A' is hydrogen
$Y_1$ and $Y_2$ are equal and signify a group of formula I, wherein
$R_a$ is methyl
$R_b$ is hydrogen or methyl and
m is 1
a group of formula 3, wherein $R_c$ is ($C_{1-6}$)alkyl
a group of formula 4, wherein
$R_d$ is hydrogen or benzyl, and
$R_e$ is ($C_{1-5}$)alkyl,
or a group of formula 5, wherein
p is 0 or 1
q is 0
r is 0
and $R_8$ and $R_9$ are both hydrogen
B is Phe or Tyr
C is —(D)Trp
D is Lys
E is Thr
F is

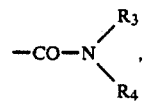

wherein
$R_3$ is hydrogen, $R_4$ is —CH($R_5$)—X, $R_5$ is CH(CH$_3$)OH, X is CH$_2$OH,
as well as the salt forms thereof.

We claim:

1. A polypeptide of formula I,

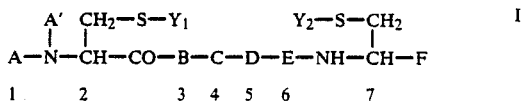

wherein A is
(a) is residue of formula Ia

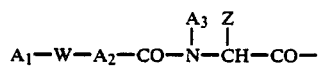

wherein
W is a group of formula

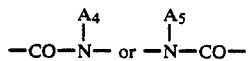

$A_1$ and $A_4$ are independently hydrogen, a saturated aliphatic $C_{1-19}$hydrocarbyl, unsaturated aliphatic $C_{2-19}$hydrocarbyl, or $C_{7-10}$phenylalkyl, wherein phenyl is optionally substituted by halogen, trifluoromethyl, nitro, hydroxy, $C_{1-3}$alkyl and/or $C_{1-3}$alkoxy, $A_5$ is hydrogen or a saturated aliphatic $C_{1-12}$hydrocarbyl or unsaturated $C_{2-12}$hydrocarbyl or $A_1+A_5$ together signify tetramethylene or pentamethylene, $A_2$ is saturated $C_{1-19}$alkylene or unsaturated $C_{2-19}$alkylene, whereby $A_1$, $A_2$ and $A_4$ together or $A_1$, $A_2$ and $A_5$ together contain 10 to 20 carbon atoms, $A_3$ is hydrogen, a saturated aliphatic $(C_{1-12})$ hydrocarbyl, a unsaturated aliphatic $(C_{2-12})$hydrocarbyl or $(C_{7-10})$phenylalkyl, wherein phenyl is optionally substituted by halogen, trifluoromethyl, nitro, hydroxy, $(C_{1-3})$alkyl or $(C_{1-3})$ alkoxy, $>N-CH(Z)-Co-$ is (1) an (L)- or (D)-phenylalanine residue optionally ring-substituted by halogen, $NO_2$, $NH_2$, OH, $C_{1-3}$alkyl and/or $C_{1-3}$alkoxy, or (2) the residue of the natural α-amino acid other than defined under (1) above, or of a corresponding (D)-amino acid, whereby Z in $>-N-CH(Z)-CO-$ represents the remainder of said residue (1) or (2);

A' is hydrogen and $Y_1$ and $Y_2$ are each hydrogen or together represent a direct bond, or (b) hydrogen, $C_{1-12}$alkyl, $C_{7-10}$phenylalkyl or RCO, R is hydrogen, $C_{1-12}$alkyl, phenyl or $C_{7-10}$phenylalkyl or RCO is (α) a (L)- or (D)-phenylalanine residue optionally ring-substituted by halogen, $NO_2$, $NH_2$, OH, $C_{1-3}$alkyl and/or $C_{1-3}$alkoxy or (β) the residue of a natural (L)-α-amino acid other than defined under (a) above, or of a corresponding (D)-amino acid or (γ) a dipeptide residue in which the individual amino acid residues are the same or different and are selected from those defined under (α) and (γ) above, the α-amino group of amino acid residues (α) and-(β) and the N-terminal amino group of dipeptide residues (γ) being optionally substituted by $C_{1-12}$alkyl or $C_{7-10}$phenylalkyl and/or $C_{1-11}$acyl, A' is hydrogen or when A is $(C_{1-12})$alkyl or $(C_{7-10})$-phenylalkyl, then A' can also signify $(C_{1-12})$ alkyl whereby the total number of carbon atoms of A+A' does not exceed 13 carbon atoms, $Y_1$ and $Y_2$ are independently a group of formula 1, 2, 3, 4 or 5,

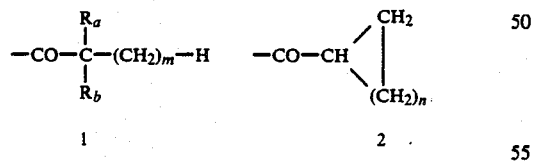

1    2

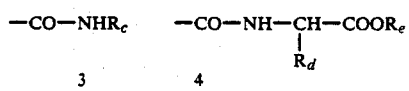

3    4

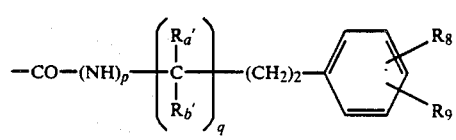

5 wherein $R_a$ is methyl or ethyl, $R_b$ is hydrogen, methyl or ethyl, m is 1, 2, 3, 4 or n is 1, 2, 3, 4 or 5

$R_c$ is $(C_{1-6})$alkyl $R_d$ represents the substituent attaching to the α-carbon atom of a natural α-amino acid (including hydrogen)

$R_e$ is $(C_{1-5})$alkyl $R_a'$ and $R_b'$ are independently hydrogen, methyl or ethyl, $R_8$ and $R_9$ are independently hydrogen, halogen, $(C_{1-3})$ alkyl or $(C_{1-3})$alkoxy, p is 0 or 1, q is 0 or 1, r is 0, 1 or 2, and for both cases (a) and (b)

B is —Phe— optionally ring-substituted by halogen, $NO_2$, $NH_2$, OH, $C_{1-3}$alkyl and/or $C_{1-3}$alkoxy, C is (L)—Trp— or (D)—Trp— optionally α-N-methylated and optionally benzene-ring-substituted by halogen, $NO_2$, $NH_2$. OH, $C_{1-3}$alkyl and/or $C_{1-3}$alkoxy, D is —Lys— optionally α-N-methylated, E is Thr, Ser or Val F is a group of formula —COOR$_1$, —CH$_2$OR$_2$,

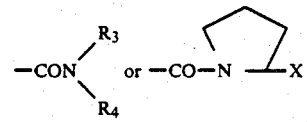

wherein $R_1$ is hydrogen or $C_{1-3}$alkyl, $R_2$ is hydrogen or the residue of a physiologically acceptable, physiologically hydrolysable ester, $R_3$ is hydrogen, $C_{1-3}$alkyl, phenyl or $C_{7-10}$phenylalkyl, but when $R_4$ is —CH(R$_5$)—X then $R_3$ is only hydrogen or methyl, $R_4$ is hydrogen, $C_{1-3}$alkyl or a group of formula —CH(R$_5$)—X, $R_5$ is hydrogen, —(CH$_2$)$_2$—OH or —(CH$_2$)$_3$—OH, or represents the substituent attaching to the α-carbon atom of a natural α-amino acid and X is a group of formula —COOR$_1$, —CH$_2$OR$_2$ or

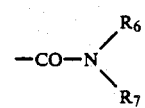

wherein $R_1$ and $R_2$ have the meanings given above, $R_6$ is hydrogen or $C_{1-3}$alkyl and $R_7$ is hydrogen, $C_{1-3}$alkyl, phenyl or $C_{7-10}$phenylalkyl, whereby the residues B, D and E have the L-configuration, and the residues in the 2- and 7-position and the residues ($Y_14$) and ($Y_24$) each independently have the (L)- or (D)-configuration, as well as the salt forms and complexes thereof.

2. A polypeptide according to claim 1, wherein A, A', $Y_1$ and $Y_2$ have the meanings given under (a) in claim 1, as well as the salt forms and complexes thereof.

3. A polypeptide according to claim 1, wherein A, A', $Y_1$ and $Y_2$ have the meanings given under (b) in claim 1, as well as the salt forms and complexes thereof.

4. A compound according to claim 1 wherein A is residue of formula Ia, wherein
W is a group of formula

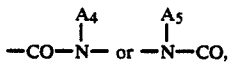

$A_1$ is saturated aliphatic $C_{1-19}$hydrocarbyl or $C_{7-10}$phenylalkyl
$A_4$ is hydrogen or saturated aliphatic $C_{1-19}$hydrocarbyl
$A_5$ is hydrogen or saturated aliphatic $C_{1-12}$hydrocarbyl
$A_2$ is saturated $C_{1-19}$alkylene
$A_3$ is hydrogen
$>$—N—CH(Z)—CO— is (D)-phenylalanine residue
A' is hydrogen
$Y_1$ and $Y_2$ together represent a direct bond
B is Phe
C is —(D)Trp
D is Lys
E is Thr
F is

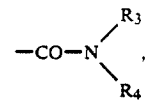

wherein
$R_3$ is hydrogen
$R_4$ is —CH($R_5$)—X,
$R_5$ is CH(CH$_3$)OH
X is CH$_2$OH
as well as the salt forms thereof.

5. A compound according to claim 1 wherein
A is RCO, wherein R is $C_{7-10}$phenylalkyl or A is (D)-phenylalanine
A' is hydrogen
$Y_1$ and $Y_2$ are equal and signify
 a group of formula 1, wherein
  $R_a$ is methyl
  $R_b$ is hydrogen or methyl and
  m is 1
 a group of formula 3, wherein $R_c$ is ($C_{1-6}$)alkyl
 a group of formula 4, wherein
  $R_d$ is hydrogen or benzyl, and
  $R_e$ is ($C_{1-5}$)alkyl,
 or a group of formula 5, wherein
  p is 0 or 1
  q is 0
  r is 0
  and $R_8$ and $R_9$ are both hydrogen
B is Phe or Tyr
C is —(D)Trp
D is Lys
E is Thr
F is

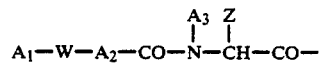

wherein $R_3$ is hydrogen, $R_4$ is —CH($R_5$)—X, $R_5$ is CH(CH$_3$)OH, X is CH$_2$OH,
as well as the salt forms thereof.

6. A compound according to claim 1 of formula

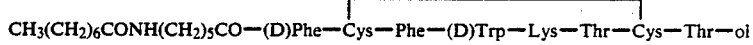

CH$_3$(CH$_2$)$_6$CONH(CH$_2$)$_5$CO—(D)Phe—Cys—Phe—(D)Trp—Lys—Thr—Cys—Thr—ol as well as the salt forms and complexes thereof.

7. A polypeptide according to claim 1 of the formula:

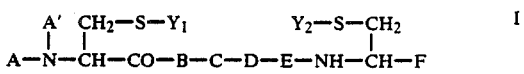

wherein
A is a residue of formula Ia

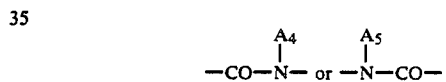

wherein W is a group of formula $$-CO-\underset{\underset{A_4}{|}}{N}- \text{ or } -\underset{\underset{A_5}{|}}{N}-CO-$$

$A_1$ and $A_4$ are independently hydrogen, a saturated aliphatic $C_{1-19}$hydrocarbyl, unsaturated aliphatic $C_{2-19}$hydrocarbyl, or $C_{7-10}$phenylalkyl, wherein phenyl is optionally substituted by halogen, trifluoromethyl, nitro, hydroxy, $C_{1-3}$alkyl and/or $C_{1-3}$alkoxy,
$A_5$ is hydrogen or a saturated aliphatic $C_{1-12}$hydrocarbyl or unsaturated $C_{2-12}$hydrocarbyl or
$A_1 + A_5$ together signify tetramethylene or pentamethylene,
$A_2$ is saturated $C_{1-19}$alkylene or unsaturated $C_{2-19}$alkylene, whereby $A_1$, $A_2$ and $A_4$ together or $A_1$, $A_2$ and $A_5$ together contain 10 to 20 carbon atoms,
$A_3$ is hydrogen, a saturated aliphatic ($C_{1-12}$) hydrocarbyl, a unsaturated aliphatic ($C_{2-12}$)hydrocarbyl or ($C_{7-10}$)phenylalkyl, wherein phenyl is optionally substituted by halogen, trifluoromethyl, nitro, hydroxy, ($C_{1-3}$)alkyl or ($C_{1-3}$)alkoxy,
$>$N—CH(Z)—CO— is
(1) an (L)- or (D)-phenylalanine residue optionally ring-substituted by halogen, NO$_2$, NH$_2$, OH, $C_{1-3}$alkyl and/or $C_{1-3}$alkoxy, or
(2) the residue of a natural α-amino acid other than defined under (1) above, or of a corresponding (D)-amino acid,
whereby Z in $>$—N—CH(Z)—CO— represents the remainder of said residue (1) or (2),
A' is hydrogen and
$Y_1$ and $Y_2$ are each hydrogen or together represent a direct bond, B is —Phe— optionally ring-substituted by halogen, $NO_2$, $NH_2$, OH, $C_{1-3}$alkyl and/or $C_{1-3}$alkoxy, C is (L)—Trp— or (D)—Trp— optionally α-N-methylated and optionally benzene-ring-substituted by halogen, $NO_2$, $NH_2$, OH, $C_{1-3}$alkyl and/or $C_{1-3}$alkoxy, D is —Lys— optionally α-N-methylated, E is Thr, Ser or Val F is a group of formula —$COOR_1$, —$CH_2OR_2$,

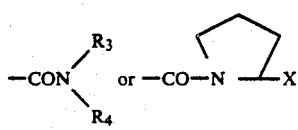

wherein $R_1$ is hydrogen or $C_{1-3}$alkyl, $R_2$ is hydrogen or the residue of a physiologically acceptable, physiologically hydrolysable ester, $R_3$ is hydrogen, $C_{1-3}$alkyl, phenyl or $C_{7-10}$phenylalkyl, but when $R_4$ is —$CH(R_5)$—X then $R_3$ is only hydrogen or methyl, $R_4$ is hydrogen, $C_{1-3}$alkyl or a group of formula —$CH(R_5)$—X, $R_5$ is hydrogen, —$(CH_2)_2$—OH or —$(CH_2)_3$—OH, or represents the substituent attaching to the α-carbon atom of a natural α-amino acid and X is a group of formula —$COOR_1$, —$CH_2OR_2$ or

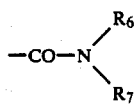

wherein $R_1$ and $R_2$ have the meanings given above, $R_6$ is hydrogen or $C_{1-3}$alkyl and $R_7$ is hydrogen, $C_{1-3}$alkyl, phenyl or $C_{7-10}$phenylalkyl, whereby the residues B, D and E have the L-configuration, and the residues in the 2- and 7-position each independently have the (L)- or (D)-configuration, or a pharmaceutically acceptable salt form or complex thereof.

8. A polypeptide according to claim 1 of the formula:

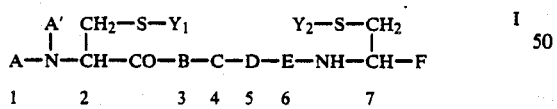

wherein

A is hydrogen, $C_{1-12}$alkyl, $C_{7-10}$phenylalkyl or RCO,

R is hydrogen, $C_{1-12}$alkyl, phenyl or $C_{7-10}$ phenylalkyl or

RCO is (α) a (L)- or (D)-phenylalanine residue optionally ring-substituted by halogen, $NO_2$, $NH_2$, OH, $C_{1-3}$alkyl and/or $C_{1-3}$alkoxy or (β) the residue of a natural (L)-α-amino acid other than defined under (a) above, or of a corresponding (D)-amino acid or (γ) a dipeptide residue in which the individual amino acid residues are the same or different and are selected from those defined under (α) and (β) above, the α-amino group of amino acid residues (α) and (β) and the N-terminal amino group of dipeptide residues (γ) being optionally substituted by $C_{1-12}$alkyl or $C_{7-10}$phenylalkyl and/or $C_{1-11}$acyl, A' is hydrogen or when A is ($C_{1-12}$)alkyl or ($C_{7-10}$)-phenylalkyl, then A' can also signify ($C_{1-12}$)alkyl whereby the total number of carbon atoms of A+A' does not exceed 13 carbon atoms, $Y_1$ and $Y_2$ are independently a group of formula 1, 2, 3, 4 or 5,

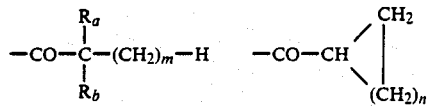

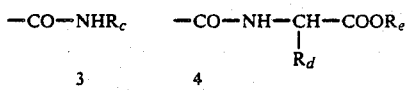

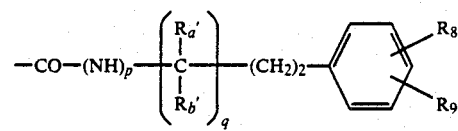

wherein $R_a$ is methyl or ethyl, $R_b$ is hydrogen, methyl or ethyl, m is 1, 2, 3, 4 or n is 1, 2, 3, 4 or 5

$R_c$ is ($C_{1-6}$)alkyl $R_d$ represents the substituent attaching to the α-carbon atom of a natural α-amino acid (including hydrogen)

$R_e$ is ($C_{1-5}$)alkyl $R_a'$ and $R_b'$ are independently hydrogen, methyl or ethyl, $R_8$ and $R_9$ are independently hydrogen, halogen, ($C_{1-3}$)alkyl or ($C_{1-3}$)alkoxy, p is 0 or 1, q is 0 or 1, r is 0, 1 or 2, B is —Phe— optionally ring-substituted by halogen, $NO_2$, $NH_2$, OH, $C_{1-3}$alkyl and/or $C_{1-3}$alkoxy, C is (L)—Trp— or (D)—Trp— optionally α-N-methylated and optionally benzene-ring-substituted by halogen, $NO_2$, $NH_2$, OH, $C_{1-3}$alkyl and/or $C_{1-3}$alkoxy, D is —Lys— optionally α-N-methylated, E is Thr, Ser or Val F is a group of formula —$COOR_1$, —$CH_2OR_2$,

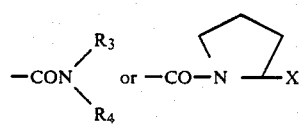

wherein $R_1$ is hydrogen or $C_{1-3}$alkyl, $R_2$ is hydrogen or the residue of a physiologically acceptable, physiologically hydrolysable ester, $R_3$ is hydrogen, $C_{1-3}$alkyl, phenyl or $C_{7-10}$phenylalkyl, but when $R_4$ is —CH($R_5$)—X then $R_3$ is only hydrogen or methyl, $R_4$ is hydrogen, $C_{1-3}$alkyl or a group of formula —CH($R_5$)—X, $R_5$ is hydrogen, —(CH$_2$)$_2$—OH or —(CH$_2$)$_3$—OH, or represents the substituent attaching to the α-carbon atom of a natural α-amino acid and X is a group of formula —COOR$_1$, —CH$_2$OR$_2$ or

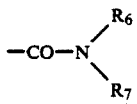

wherein $R_1$ and $R_2$ have the meanings given above, $R_6$ is hydrogen or $C_{1-3}$alkyl and $R_7$ is hydrogen, $C_{1-3}$alkyl, phenyl or $C_{7-10}$phenylalkyl, whereby the residues B, D and E have the L-configuration, and the residues in the 2- and 7-position and the residues (Y$_1$4) and (Y$_2$4) each independently have the (L)- or (D)-configuration.

9. A method of treating disorders with an aetiology comprising or associated with excess GH-secretion or gastro intestinal disorders which comprise administering a compound of claim 1 or a pharmaceutically acceptable salt or complex thereof in an amount effective for the treatment of said disorders.

10. A pharmaceutical composition useful in treating disorders with an aetiology comprising or associated with excess GH-secretion or gastro intestinal disorders comprising a compound of Formula I as defined in claim 1 or a pharmaceutically acceptable salt or a complex thereof in an amount effective for the treatment of said disorders and a pharmaceutically acceptable diluent or carrier therefor.

* * * * *